United States Patent [19]

Hauser et al.

[11] Patent Number: 5,582,590
[45] Date of Patent: Dec. 10, 1996

[54] FLOW CONTROL DEVICE FOR INFUSION SYSTEMS

[76] Inventors: Jean-Lue Hauser, 1499 chemin S. Maymes, F - 06600 Antibes; Daniel Guyomar, 185 avenue Fabron, F - 06200 Nice; Jean D. Sauzade, Commanderie St. Christophe, F-06130 Grasse, all of France

[21] Appl. No.: 170,205

[22] PCT Filed: Apr. 28, 1993

[86] PCT No.: PCT/FR93/00410

§ 371 Date: Jun. 9, 1994

§ 102(e) Date: Jun. 9, 1994

[87] PCT Pub. No.: WO93/21977

PCT Pub. Date: Nov. 11, 1993

[30] Foreign Application Priority Data

Apr. 29, 1992 [FR] France ................ 92 05305

[51] Int. Cl.⁶ ............................................. A61M 5/00
[52] U.S. Cl. ............................................. 604/30
[58] Field of Search ................... 604/30, 31, 33, 604/34, 246, 247, 249, 250, 251, 255; 251/129.06

[56] References Cited

U.S. PATENT DOCUMENTS

| | | | |
|---|---|---|---|
| 3,063,422 | 11/1962 | Gregowski et al. | 251/129.06 |
| 4,038,981 | 8/1977 | LeFevre et al. | |
| 4,142,553 | 3/1979 | Sakakibara et al. | |
| 4,340,083 | 7/1982 | Cummins | 251/129.06 |
| 4,616,801 | 10/1986 | Cewers et al. | |
| 4,617,952 | 10/1986 | Fijiwara et al. | 251/129.06 |
| 4,623,331 | 11/1986 | Cewers et al. | |
| 4,705,059 | 11/1987 | Lecerf et al. | |
| 4,787,071 | 11/1988 | Kreuter et al. | 251/129.06 |
| 5,203,537 | 4/1993 | Jacobs et al. | 251/129.06 |
| 5,343,894 | 9/1994 | Frisch et al. | 251/129.06 |
| 5,354,032 | 10/1994 | Sim et al. | 251/129.06 |

FOREIGN PATENT DOCUMENTS

| | | | |
|---|---|---|---|
| 0205381 | 12/1986 | European Pat. Off. | |
| 2642812 | 8/1990 | France | 251/129.06 |
| 3507106 | 9/1986 | Germany. | |
| 403234981A | 10/1991 | Japan | 251/129.06 |
| 0608011 | 5/1978 | U.S.S.R. | 251/129.06 |
| 1036963 | 8/1983 | U.S.S.R. | 251/129.06 |
| 1109543 | 8/1984 | U.S.S.R. | 251/129.06 |
| 1593495 | 7/1981 | United Kingdom. | |
| 2225133 | 5/1990 | United Kingdom | 251/129.06 |

*Primary Examiner*—Manuel Mendez
*Attorney, Agent, or Firm*—F. A. Sirr; E. C. Hancock; Holland & Hart llp

[57] ABSTRACT

A device for controlling the flow of a medicinal substance in an infusion tube by means of a valve comprising a sealing means and a circuit (24) for controlling the position of the sealing means. The valve includes a chamber (10) with an inlet (12) and an outlet (14), a bi-metallic strip (16) arranged within the chamber (10) and secured to one of its walls (18), a ball (20) secured to the bi-metallic strip (16) for partially or entirely sealing off the inlet (12), and a control circuit (24) for controlling the voltages (V1, V2) applied to said strip (16) in order to provided continuous and accurate control of the flow of medicinal substance through the valve.

3 Claims, 1 Drawing Sheet

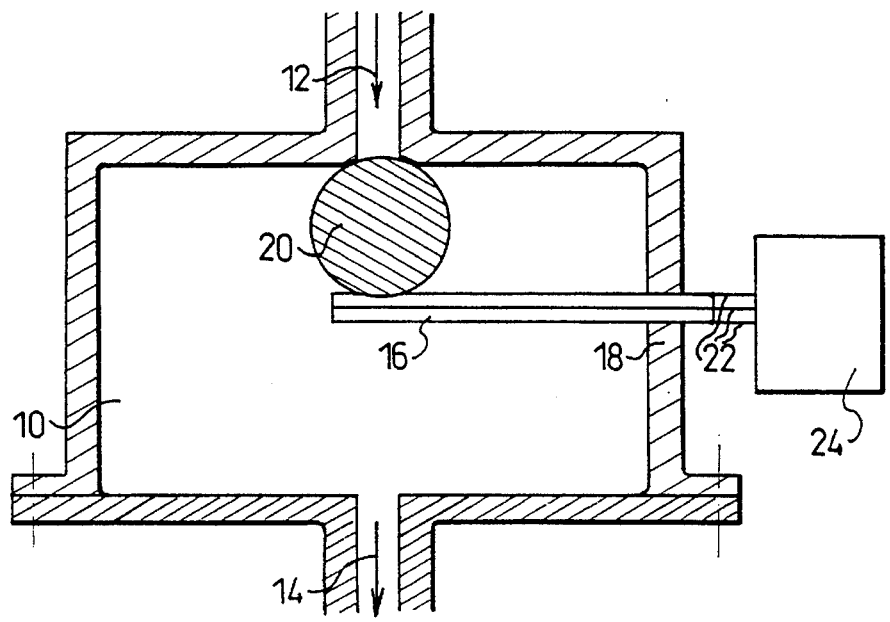
FIG·1
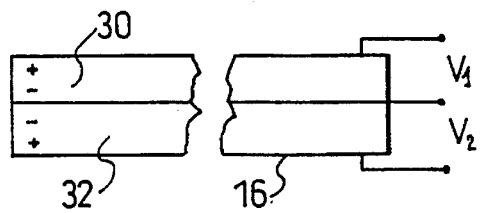
FIG·2
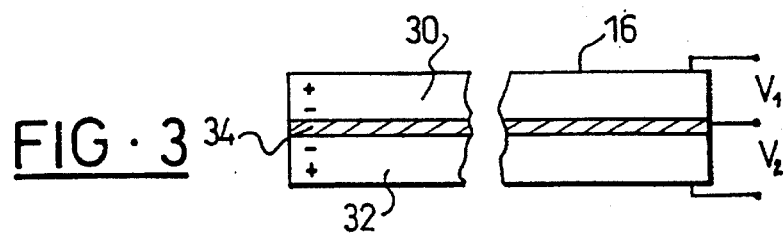
FIG·3

FLOW CONTROL DEVICE FOR INFUSION SYSTEMS

BACKGROUND OF THE INVENTION

1. Field of the Invention

This invention concerns a flow control device for therapeutic solutions in a infusion line of a type including a valve with a seal for the infusion line and a circuit for controlling the position of the seal in order to control the flow of therapeutic solution through the valve.

2. Description of Prior Art

Treatment for a certain number of illnesses, such as diabetes, cancer, etc., using chemotherapy requires the practice of infusion on a continuous or intermittent basis, for the purpose of administering one or more therapeutic solutions to the patient.

Infusion systems may be either fixed, generally in a hospital setting, where the flow of therapeutic solution is gravitational, for instance from a plastic bag suspended above the patient's bed, or portable, using a pump carried by the patient for automatic injection of the therapeutic solution into the patient's body. Whichever of these infusion systems is used, it is sometimes necessary to improve the efficiency and safety of the system by adding a flow control device.

Earlier techniques relied on various means for controlling the flow of therapeutic solution. Thus, U.S. Pat. No. 4,623,331 describes a infusion system using a suspended bag in which an alarm is set off when an incorrect number of drops is delivered by the infusion line. This is not truly a flow control device, but rather a simple security device.

U.S. Pat. No. 4,616,801 describes a system using an eccentric roller to compress the infusion line by electrically controlled rotation. The degree of compression modulates the flow. Obviously, the precision of such a system can only be approximate.

U.S. Pat. No. 4,038,981 describes a infusion line with an electromagnetic ball valve for regulating the number of drops over time, setting a minimum and maximum number of drops. The sole purpose of the electromagnetic control of the valve is to raise or lower the ball, i.e., open or close the valve. This system clearly does not provide constant flow control of the therapeutic solution but only counts the number of drops supplied, without any possibility of controlling the volume of each drop.

SUMMARY OF THE INVENTION

The purpose of this invention is to achieve constant control of the flow of therapeutic solution in a infusion line.

The invention is a flow control device with electrically controlled valve as will described, in which the valve includes a chamber with a first aperture communicating with the upstream part of the infusion line and a second aperture communicating with the downstream part of the infusion line, a bimetal device inside the chamber, a ball attached to the bimetal device to close one of the apertures in the chamber in whole or in part and a control circuit outside the chamber connected to the bimetal device for constant accurate control of the flow of therapeutic solution in the infusion line.

BRIEF DESCRIPTION OF THE DRAWINGS

The invention will be better understood through the description below, in reference to the figures, in which:

FIG. 1 represents a section of a preferred means of making the control device according to the invention, FIG. 2 represents a section of a first type of piezoelectric bimetal strip to be used in the control device according to the invention, FIG. 3 represents a section of a second type of piezoelectric bimetal strip to be used in the control device according to the invention.

DESCRIPTION OF THE PREFERRED EMBODIMENTS

As illustrated in FIG. 1, the infusion line includes a chamber 10 communicating with the input of the infusion line by aperture 12 and communicating with the output of the infusion line by aperture 14. The piezoelectric-type bimetal device 16 is set in one of the sides 18 of chamber 10. A ball 20 is attached to bimetal strip 16 so that, when bimetal strip 16 is in resting position, the ball closes input aperture 12 of the infusion line.

The bimetal device is connected by a 3-wire connection 22 to control circuit 24 which applies voltages to each of the bimetal strip's two blades so the upper blade is extended while the lower blade retracts, as specified below. This bimetal strip is forced to bend, pulling ball 20 downward, to open input aperture 12. The extent to which bimetal strip 16 bends depends on the voltage applied to input lines 22 by control circuit 24, thereby adjusting the flow of therapeutic solution with great accuracy.

Although the favoured seal for aperture 12 is ball 20, it is obvious to a professional that this seal could have any other appropriate form, such as a cone, a disk or even a dissymetrically shaped surface. However, it is clear that the ball has the advantage over any other seal in that it adapts easily to its seat and provides good accuracy mainly for small amounts of flow, which is not the case for any other form of seal.

It is also clear that flow control could also be obtained by sealing output aperture 14 rather than by sealing input aperture 12. In this case bimetal strip 16 should be adapted to bend upward, in the version shown in FIG. 1, to increase the flow of therapeutic solution. Finally, it is possible to foresee that, when at rest, ball 20 or any other appropriate seal does not entirely seal aperture 12 (or 14) but leaves a partial opening so flow is not reduced to zero in case of failure in the application of voltages by control circuit 24.

FIG. 2 shows one version of piezoelectric bimetal device 16 of the invention. Bimetal strip 16 is made up of two polarized blades, 30 and 32, made of piezoelectric material. The two blades have a metal coating on both outer faces, as well as their common face, so the application of voltage V1 to blade 30 and V2 to blade 32 is uniform along the entire blade. Combining the two appropriate voltages, V1 and V2, causes extension of blade 30 and contraction of blade 32, so the bimetal device curves downward (or upward). Thus, the appropriate voltages for V1 and V2 are between 0 and 20 volts. One of these voltages may for instance vary according to desired flow, the other voltage being set at 20 volts; or each voltage may vary between 0 and 20 volts, using only the difference between voltages to control flow.

Since the bimetal device is in the perfused liquid, it should be made of a material that remains highly stable and reliable, i.e., its response remains identical whatever the perfused liquid, within a temperature range of 10° C. to 25° C. Moreover, and this is one of the characteristics of the invention, response time for the bimetal device must be as short as possible. These characteristics may be obtained by using preferably piezoelectric ceramic or any other material with equivalent characteristics.

Obviously, the flow control device according to the invention must be calibrated before any use in the infusion medium. Calibration may be performed with water at a temperature between 15° C. and 20° C.

A second way of making bimetal device 16 is shown in FIG. 3. In this example, a metal strip 34 is set between the two blades 30 and 32. This metal strip is of course thicker than a simple metal coating as illustrated in FIG. 2. The advantage of using a metal strip between the two blades of piezoelectric material is to reinforce the rigidity of the bimetal strip and improve the accuracy of flow control. Another possible alternative (not shown) would involve using only one active blade controlled by variable voltage, the other being passive, for instance a simple grounded metal blade.

Control circuit 24 for applying control voltages V1 and V2 to the bimetal strip in fact receives current from the blades, whose intensity helps control the state of stress in the bimetal strip. Voltages V1 and V2 could then be determined in terms of the currents received on wires 22, and circuit 24 could then be a circuit of a type in which generating the voltages V1 and V2 applied to the bimetal strip depends on the currents measured at the output of wires 22. This type of circuit is easy for professionals to manage and thus not shown in the figures.

Moreover, the control circuit may take the form of an autonomous circuit including input for programming the desired flow of therapeutic solution, or connected to a centralized control system, such as a portable programmable pumping device, where flow conditions could then be programmed through the programmable pumping device. Similarly, control circuit 24 may be connected to a pressure sensor located upstream in the infusion line, to adjust flow according to pressure in the infusion line.

We claim:

1. Apparatus for controlling the flow of a therapeutic solution through an infusion line, comprising;

a closed chamber having an inlet aperture and an outlet aperture, an infusion line having an upstream portion and a downstream portion, said upstream portion being connected to said inlet aperture and adapted to connect said inlet aperture to a source of therapeutic solution, said downstream portion being connected to said outlet aperture and adapted to receive a therapeutic solution from said chamber, a bimetal device having a first portion located within said chamber and having a second portion located outside of said chamber, a ball-shaped valve member attached to said first portion of said bimetal device in a manner to cooperate with said first aperture, and voltage control means connected to said second portion of said bimetal device for variably controlling a current flow through said first portion of said bimetal device, said current flow operating to cause said first portion of said bimetal device to bend a variable amount in accordance with a magnitude of said current flow, said first portion of said bimetal device thereby operating to variably control the position of said ball-shaped valve member relative to said first aperture, so as to variably seal said first aperture and thereby variably control flow of said therapeutic solution from said upstream portion to said downstream portion in accordance with said magnitude of current flow through said first portion of said bimetal device.

2. The apparatus of claim 1 wherein said bimetal device comprises two blades of piezoelectric material having a metal strip located between said two blades, and wherein said voltage control means applies a first voltage between said metal strip and one of said two blades and applies a second voltage between said metal strip and the other of said two blades.

3. A method for controlling the flow of a therapeutic solution through an infusion line, comprising;

providing a closed chamber having an inlet aperture and an outlet aperture, providing an infusion line having an upstream portion and a downstream portion, connecting said upstream portion of said infusion line to said inlet aperture, connecting said downstream portion to said outlet aperture, providing a bimetal device having a first portion located within said chamber and having a second portion located outside of said chamber, attaching a ball-shaped valve member to said first portion of said bimetal device in a manner to cooperate with said first aperture, and connecting voltage control means to said second portion of said bimetal device for variably controlling current flow through said first portion of said bimetal device and thereby variably controlling the position of said ball-shaped valve member relative to said first aperture.

* * * * *